(12) United States Patent
Yu et al.

(10) Patent No.: US 11,406,304 B2
(45) Date of Patent: *Aug. 9, 2022

(54) SYSTEMS AND METHODS FOR PHYSIOLOGICAL SIGN ANALYSIS

(71) Applicant: Vita-Course Technologies Co., Ltd., Shenzhen (CN)

(72) Inventors: Jiao Yu, Shenzhen (CN); Jiwei Zhao, Shenzhen (CN); Zhiyong Wang, Shenzhen (CN)

(73) Assignee: VITA-COURSE TECHNOLOGIES CO., LTD., Shenzhen (CN)

( * ) Notice: Subject to any disclaimer, the term of this patent is extended or adjusted under 35 U.S.C. 154(b) by 171 days.

This patent is subject to a terminal disclaimer.

(21) Appl. No.: 15/567,975

(22) PCT Filed: Apr. 20, 2015

(86) PCT No.: PCT/CN2015/077025
§ 371 (c)(1),
(2) Date: Oct. 20, 2017

(87) PCT Pub. No.: WO2016/168979
PCT Pub. Date: Oct. 27, 2016

(65) Prior Publication Data
US 2018/0132744 A1    May 17, 2018

(51) Int. Cl.
*A61B 5/316*   (2021.01)
*A61B 5/00*    (2006.01)
(Continued)

(52) U.S. Cl.
CPC .............. *A61B 5/316* (2021.01); *A61B 5/318* (2021.01); *A61B 5/7203* (2013.01);
(Continued)

(58) Field of Classification Search
None
See application file for complete search history.

(56) References Cited

U.S. PATENT DOCUMENTS 5,469,858 A * 11/1995 Osborne ................ A61B 5/333
600/523
5,622,178 A     4/1997 Gilham
(Continued)

FOREIGN PATENT DOCUMENTS

CA      2346243 A1    11/2002
CN    101088456 A    12/2007
(Continued)

OTHER PUBLICATIONS

International Search Report in PCT/CN2015/077025 dated January 7, 2016, 7 pages.
(Continued)

*Primary Examiner* — Michael W Kahelin
*Assistant Examiner* — Elizabeth K So
(74) *Attorney, Agent, or Firm* — Metis IP LLC

(57) ABSTRACT

The present disclosure relates to systems and methods for analyzing physiological sign information, including information acquisition, data storage, calculation or analysis, processing, result output, etc. The systems may perform a calculation or an analysis on the acquired information by a plurality of algorithms, perform a determination or a processing on the calculation result, and output the determination result of the processed physiological information.

12 Claims, 9 Drawing Sheets

(51) Int. Cl.
*A61B 5/318* (2021.01)
*A61B 5/349* (2021.01)
*G16H 50/30* (2018.01)

(52) U.S. Cl.
CPC .......... *A61B 5/7264* (2013.01); *A61B 5/7275* (2013.01); *A61B 5/0004* (2013.01); *A61B 5/349* (2021.01); *A61B 5/7207* (2013.01); *A61B 5/7217* (2013.01); *G16H 50/30* (2018.01)

(56) References Cited

U.S. PATENT DOCUMENTS

| | | | |
|---|---|---|---|
| 5,758,654 A * | 6/1998 | Burton-Krahn | A61B 5/349 600/517 |
| 8,285,369 B2 | 10/2012 | Kuo et al. | |
| 8,433,395 B1 | 4/2013 | Brockway et al. | |
| 8,632,465 B1 | 1/2014 | Brockway | |
| 8,825,145 B1 | 9/2014 | Zhang | |
| 2004/0049106 A1 | 3/2004 | Kanazawa | |
| 2005/0234363 A1 | 10/2005 | Xue | |
| 2008/0002775 A1 | 1/2008 | Ricci et al. | |
| 2009/0143693 A1 | 6/2009 | Ye et al. | |
| 2010/0106038 A1 | 4/2010 | Schmidt et al. | |
| 2014/0128758 A1 | 5/2014 | Galloway et al. | |
| 2015/0094552 A1 | 4/2015 | Golda et al. | |
| 2015/0283387 A1* | 10/2015 | Sun | A61N 1/3702 607/27 |

FOREIGN PATENT DOCUMENTS

| | | | |
|---|---|---|---|
| CN | 101467879 A | 7/2009 | |
| CN | 101683260 A | 3/2010 | |
| CN | 101799974 A | 8/2010 | |
| CN | 101953682 A | 1/2011 | |
| CN | 102697492 A | 10/2012 | |
| CN | 10386012 B2 * | 12/2012 | ........... A61N 1/3702 |
| CN | 102988041 A | 3/2013 | |
| CN | 103083013 A | 5/2013 | |
| CN | 103405227 A | 11/2013 | |
| CN | 104102915 A | 10/2014 | |
| CN | 104182625 A | 12/2014 | |
| CN | 104305991 A | 1/2015 | |
| CN | 104367316 A | 2/2015 | |
| WO | 2013043157 A2 | 3/2013 | |

OTHER PUBLICATIONS

Written Opinion of the International Searching Authority for PCT/CN2015/077025 dated Jan. 7, 2016, 12 pages.
First Office Action in Chinese Application No. 201580078360.6 dated Nov. 26, 2010, 22 pages.
International Search Report in PCT/CN2015/077026 dated Jan. 21, 2016, 8 Pages.
Written Opinion in PCT/CN2015/077026 dated Jan. 21. 2016, 8 Pages.
Second Office Action in Chinese Application No. 201580078360.6 dated Sep. 1, 2020, 15 pages.

\* cited by examiner

SYSTEMS AND METHODS FOR PHYSIOLOGICAL SIGN ANALYSIS

CROSS-REFERENCE TO RELATED APPLICATIONS

The present application is a U.S. national stage under 35 U.S.C. § 371 of International Application No. PCT/CN2015/077025, filed on Apr. 20, 2015, designating the United States of America, which is related to a PCT application entitled "PHYSIOLOGICAL SIGN INFORMATION ACQUISITION METHOD AND SYSTEM" filed on Apr. 20, 2015, the entire contents of which are hereby incorporated by reference.

TECHNICAL FIELD

The present disclosure generally relates to systems and methods for acquiring, processing, extracting, and analyzing physiological sign information.

BACKGROUND

A living body includes a lot of life information all the time. The life information may be summarized into two categories: chemical information (chemical components that constitute the living body and information relating to its changes) and physical information (locations, shapes, relative relationships of organs in the living body, and force, heat, sound, light, and other related information generated by movement of the living body). A circulatory system formed by heart and vessels of some animals may constitute a blood circulation and may be one of the most important organs and components for the animals. The chemical information and physical information of a cardiovascular system contain a large amount of information.

Heart disease is a common chronic disease. Because the status of heart disease is often hidden and develops slowly, and the morbidity risk is relatively high, heart disease has becomes a principal life-threatening disease. Heart disease has becomes the "No. one killer" that threatens the life and health of human beings, therefore, the prevention and treatment of heart disease have become the most important problems in today's medical research. The electrocardiogram (ECG) is a main technical method used to diagnose heart disease. The potential changes between a pair of points on the body surface may be recorded as an ECG waveform.

The ECG information is an important form used to represent the potential changes on the body surface. However, the measurement of the ECG information may be affected by noises, artifacts, and data missing, which may result in a wrong analysis result. The ECG information may be affected by a plurality of noises, typically including:

1) Power frequency interference: the power frequency interference is generated because that a distribution capacitance on human body and a lead loop of click electrode are affected by an alternating current and a magnetic field. The frequency of the power frequency interference is 50 Hz (or 60 Hz) frequency and its harmonics. The interference is often shown as regular fine waves on the ECG waveform and the amplitude may reach 50% of the peak point of the ECG waveform.

2) Base-line shift: the baseline drift is caused by a poor contact of electrodes and impedance changes on the electrode-skin interface. The baseline drift is a low frequency interference and the frequency is generally less than 1 Hz. The base-line shift is often shown as slow changes similar to a sinusoid wave.

3) Electromyography (EMG) interference: the EMG interference is often caused by muscle contraction. The EMG interference is a high-frequency interference (10~100 Hz) and the amplitude is in mV level. The EMG interference is often shown as irregular rapid changes on the waveform.

4) Artifact of electrode activity: the artifact is often caused by a poor contact between the human body and the electrode or the disconnecting of the human body to be measured and the measuring system. The artifact is often shown as that the baseline of the ECG information suddenly changes similar to an ECG waveform, and the duration time may reach 100~500 milliseconds.

5) Motion/vibration interference: the motion/vibration interference may refer to that during the signal input process, a signal generator (e.g., a transmission distance of a light source, a transmission angle of the light source) may change due to movement or vibration of the subject, the light source, or the sensor, and therefore, the signal characteristics are affected and the signal may be disturbed, distorted, or submerged.

The noises or interferences mentioned above may result in that the ECG waveform is not clear or a distortion occurs, which may influence the detection or recognition of the ECG waveform.

SUMMARY

The present disclosure provides a method. The method may include: obtaining physiological information; detecting features of the physiological information based on a first approach to obtain all feature results; detecting a first feature of the physiological information based on a second approach to obtain a first feature result, wherein the second approach is different from the first approach; performing a matching and a marking between the all feature results and the first feature result; marking a second feature and a third feature near the matched position of the first feature in the all feature results; determining remainder features in the all feature results other than the first feature, the second feature, and the third feature; performing a noise determination on the remainder features; outputting a result of the noise determination.

According to an embodiment of the present disclosure, the physiological information may include electrocardiogram information.

According to an embodiment of the present disclosure, the first approach may include the following steps: determining threshold; and determining peaks and valleys within the threshold as the all feature results.

According to an embodiment of the present disclosure, the first approach may include a peak detection approach. The second approach may include a threshold technique, a template matching technique, a wavelet transform technique, and a neural network technique.

According to an embodiment of the present disclosure, the first feature result may include a QRS wave in the electrocardiogram information.

According to an embodiment of the present disclosure, the position of the first feature is a position of a QRS wave in the electrocardiogram information.

According to an embodiment of the present disclosure, the second feature and the third feature may include a P wave and a T wave in the electrocardiogram information.

The present disclosure provides another method. The method may include: determining a distribution of the physiological information; calculating a characteristic quantity of the physiological information; determining a threshold of the characteristic quantity; determining whether the physiological information includes noises based on a determination that whether the characteristic quantity is within the threshold; outputting a result of noise determination.

The present disclosure provides a system. The system may include: an acquisition module for obtaining physiological information; a feature measurement module for measuring and obtaining all feature results based on a first approach; a first feature measurement module for measuring and obtaining a first feature result, wherein the first feature measurement module is different from the feature measurement module; a matching module for matching the all feature results with the first feature result and marking a position of the first feature in the all feature results; a second feature marking module for marking a second feature near the position of the first feature; a third feature marking module for marking a third feature near the position of the first feature; a calculation and analysis module for performing a noise determination on remainder features other than the first feature, the second feature, and the third feature; an output module for outputting result of noise determination.

According to an embodiment of the present disclosure, the acquisition module may include a heartbeat collection device, an electrocardiogram detecting device, a physiological information detecting device, and an intelligent wearable device with the functions of detecting heartbeat, electrocardiogram, and physiological information.

According to an embodiment of the present disclosure, the physiological information may include the electrocardiogram information.

DETAILED DESCRIPTION

Figure 1:
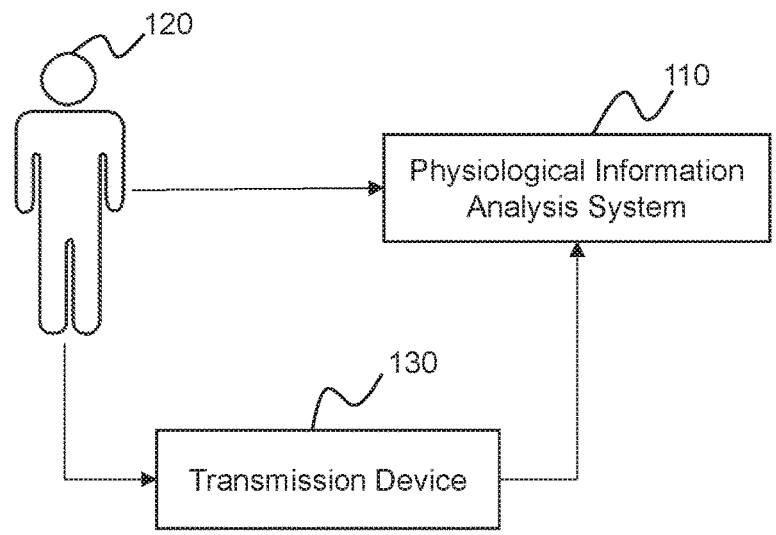
FIG. 1 illustrates an application scenario diagram of a physiological sign analysis system in the present disclosure.

According to some embodiments of the present disclosure, the physiological sign analysis system may be applied to a plurality of fields, including but not limited to, monitoring (including but not limited to old people monitoring, middle aged people monitoring, young people monitoring, early childhood monitoring, etc.), medical diagnosis (including but not limited to ECG diagnosis, pulse diagnosis, blood pressure diagnosis, blood oxygen diagnosis, etc.), motion monitoring (including but not limited to long-distance race, middle-distance race, sprint, riding, rowing, shooting, riding horse, swimming, climbing, etc.), hospital health-care (including but not limited to critical patient monitoring, patient with genetic disease monitoring, patient in emergency case monitoring, etc.), pet health-care (pet with critical illness care, newly born pet care, household pet care, etc.), etc.

The physiological sign analysis system may acquire or obtain one or more types of physiological information from a living body, for example, physical information and chemical information including ECG, pulse wave, blood pressure, blood oxygen, heart rate, body temperature, heart rate variation (HRV), blood pressure variation (BPV), brain wave, ultra low frequency radio wave, respiration, status of muscle or skeleton, blood glucose, blood fat, blood concentration, platelet content, height, weight, etc. The physiological sign analysis system may include an acquisition module configured for acquiring one or more types of physiological information; a feature measurement module configured for measuring and obtaining feature results based on a first approach; a first feature measurement module configured for measuring and obtaining a first feature result based on a second approach, wherein the feature measurement module differs from the first feature measurement module; a matching module configured for matching the feature results with the first feature result and marking a position of the first feature in the feature results; a second feature marking module configured for marking a second feature nearby the position of the first feature in the feature results; a third feature marking module configured for marking a third feature nearby the position of the first feature in the feature results; a calculation and analysis module configured for calculating or analyzing the remainder of the features other than the first feature, the second feature, and the third feature; an output module configured for outputting the calculation or analysis results. The analysis system may detect noises in the physiological information efficiently through a small amount of calculation, and perform a matching operation and a calibration operation. The system may be applied to a portable device or a wearable device conveniently. The system may monitor the physiological information in real time or in non-real time, and transmit the monitoring results to an external device (including but not limited to a storage device or a cloud server). For example, the system may monitor physiological information of a user within a random period (e.g., several minutes, several hours, several days, several months) continuously, or monitor the physiological information of the user at regular intervals. The system may display the physiological information (e.g., ECG, pulse rate, blood pressure, blood oxygen, etc.) in real time or in non-real time. The system may transmit the physiological information to a remote related third party, (e.g., a hospital, a health-care provider, or a related member). For example, the user may use the system at home and a condition of the physiological information or physiological data monitored by the system may be transmitted to a hospital, a health-care provider, or a related member. All or part of the condition of the physiological information or the physiological data may be stored in a local or remote storage device. The transmission of the physiological information mentioned above may be wired or wireless. The system may detect noises in the physiological information efficiently, and perform a matching operation and a calibration operation (therefore, the system may be applied to a portable device or a wearable device conveniently). Particularly, the system may monitor the physiological information in real time or in non-real time, and transmit the monitoring results to an external device (including but not limited to a storage device or a cloud server). The system may output and display the condition of the physiological information (e.g., ECG, pulse rate, blood pressure, blood oxygen, etc.) in real time or in non-real time. The system may transmit the physiological information to a remote related third party, (e.g., a hospital, a health-care provider, or a related member). The transmission of the physiological information mentioned above may be wired or wireless.

The descriptions above are only provided for illustration purposes, and should be not be considered as the only practical embodiment. For persons having ordinary skills in the art, after understanding the principle of the physiological information analysis system and method, may make multiple modifications and variations in the form and details of the application filed of the system and method. However, those modifications and variations are within the scope of the present disclosure.

In order to describe the technical solutions of the embodiments in the present disclosure more clearly, drawings may be described in the following detailed description. Obviously, the drawings in the following detailed description are only some embodiments of the present disclosure, persons having ordinary skills in the art may apply the drawings to other similar application scenarios without further efforts. Unless obviously obtained from the context or the context illustrates otherwise, the same numeral in the drawings refers to the same structure or process.

As used herein, the singular forms "a," "an," and "the" may be intended to include the plural forms as well, unless the context dearly indicates otherwise. It will be further understood that the terms "comprises," "comprising," "includes," and/or "including" when used in this disclosure, specify the presence of stated elements and steps, but do not preclude the presence or addition of one or more other elements and steps thereof.

FIG. 1 illustrates an application scenario diagram of a physiological sign analysis system. The application scenario may include but not limited to a physiological sign analysis system 110, a subject 120, and a transmission device 130. The physiological sign analysis system 110 may be configured to extract, receive, obtain, analyze, or process the physiological information from the subject 120. The subject 120 may include but not limited to a human body and not limited to a single living body. The physiological information may include physical information and chemical information, including but not limited to ECG, pulse wave, blood pressure, blood oxygen, heart rate, body temperature, HRV, BPV, brain wave, ultra low frequency radio wave, respiration, state of muscle or skeleton, blood glucose, blood fat, blood concentration, platelet content, height, weight, etc. The transmission device 130 may include an electric device, a mechanic device, a physical device, a chemical device, including but not limited to a processor, a sensor, an embedded device based on single chip or Advanced RISC Machines (ARM), an analysis meter, a detector, etc. The transmission mode may be wired or wireless, including but not limited to radar, infrared, Bluetooth, electric wire, optical fiber, etc. The information to be transmitted may be analog or digital, real time or non-real time. The transmission device 130 may transmit information of an independent subject, or information of a group or multiple groups of subjects. The transmission device 130 may include a central processor or a cloud server. The physiological sign analysis system 110 may acquire physiological information directly or indirectly. The physiological information acquired may be transmitted to the physiological information analysis system directly or through the transmission device 130. The physiological information may be acquired by an acquisition device including but not limited to a heartbeat acquisition device, an ECG monitor, a pulse wave monitor, a brain wave monitor, a blood pressure monitor, a physiological information monitoring device, a respiratory monitor, etc. The acquisition device may also include a wearable or portable device that may implement the functions of the devices mentioned above, including a watch, a pair of earphone, a pair of glasses, an accessory, etc. The descriptions regarding the physiological sign analysis system above are provided for illustration purposes, and should be not be considered as the only practical embodiment. For persons having ordinary skills in the art, after understanding the principle of the physiological information analysis system and method, may make multiple modifications and variations in the form and details of the application filed of the system and method. However, those modifications and variations are within the scope of the present disclosure. For example, the physiological information acquired from the subject 120 may be transmitted directly to the physiological sign analysis system 110 and not through the transmission device 130. A plurality types of physiological information acquired from a plurality of subjects may be transmitted to the physiological sign analysis system 110 to be processed. Those modifications or variations are also within the scope of the present disclosure.

Figure 2:
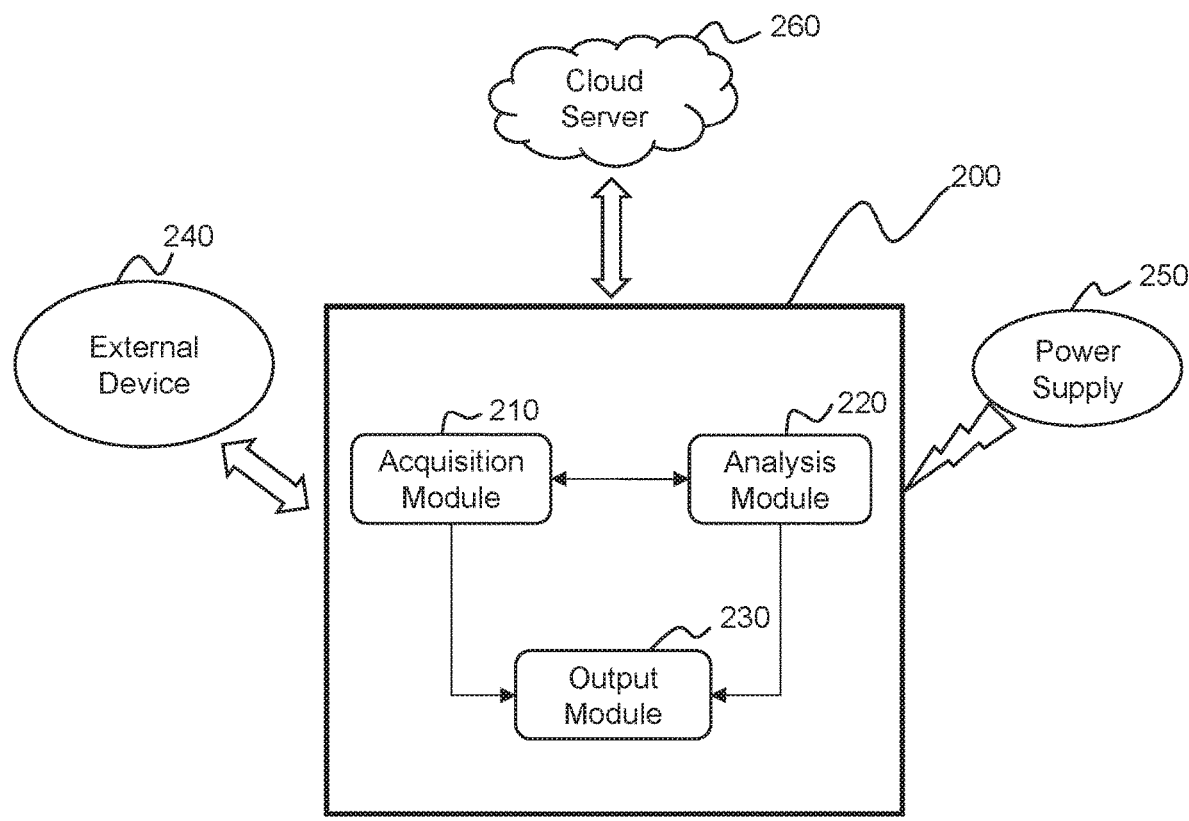
FIG. 2 illustrates a schematic diagram of the physiological sign analysis system in the present disclosure.

FIG. 2 is a schematic diagram illustrating modules in the physiological sign analysis system. The system may include, without limitations to, one or more engines 200, one or more external devices 240, one or more power supplies 250, a cloud server 260, etc. As used herein, the engine 200 may include, without limitations to, an acquisition module 210, an analysis module 220, and an output module 230. The acquisition module 210 may be configured for acquiring physiological information of a subject. The module may acquire physiological information through a photoelectrical sensing method or an electrical sensing method. The module may acquire the physiological information based on temperature change, humidity change, pressure change, body surface potential change, voltage change, current change, magnetic field variation, etc. The module may acquire information including, without limitations to, acoustic information, optical information, magnetic information, thermal information, etc. The type of the information may include ECG, heart rate, pulse rate, blood pressure, blood oxygen, respiration, etc. For example, the ECG information acquired may include, without limitations to, waveform, time interval, peak, valley, amplitude, etc. The acquisition module 210 may include one or more acquisition devices of various types. The acquisition device may be a local ECG acquisition device or a wireless remote ECG monitoring system. The acquisition device may be a clinical ECG monitoring system or a household portable ECG monitoring device. The acquisition device may be a traditional ECG monitoring device or an intelligent wearable device (e.g., a smartwatch, an earphone, etc.) that may be used to implement the function. The acquisition module 210 may acquire physiological information in a complete cycle or in a certain time interval (e.g., a time window of 4 s).

The acquisition module 210 may include an integrated calibration module or the engine 200 may include an independent calibration module (not shown). The calibration module may be configured for adjusting, optimizing, calibrating, and processing the acquired physiological information, or eliminating interferences of irrelevant information. Generally, the information acquisition process may be affected by a plurality of factors, and the factors may affect features of the physiological information including waveform, peak amplitude, peak-to-peak interval, etc. For example, the physiological information of a specific subject may be different at different times of a day. The physiological information of a specific subject may be different under different situations, for example, motion status, resting status, overload working condition, sleep status, pleasant feeling status, angry status, taking medicine or not, etc. Additionally, the physiological information of different subjects may be different even though they are under the same situation. Therefore, a calibration module may be integrated in the acquisition module 210 or in the engine 200 and may be used for adjusting, optimizing, calibrating, or eliminating interferences mentioned above to obtain more accurate physiological information. Additionally, the acquisition module 210 may adjust different parameters for different subjects and store physiological information acquired from a same subject in the cloud server 260, further, the acquisition module 210 may be adaptive which may generate a personalized physiological information database for the subject, which improves the acquisition accuracy. Additionally, a photoelectrical sensing may be affected by a plurality of factors, for example, light intensity, skin color, skin roughness, skin temperature, skin humidity, ambient temperature, ambient humidity, etc.

Therefore, an environment adaptation module may be integrated in the acquisition module 210, for example, a correction module or a compensation module corresponding to the environmental factors. The modification, variation, or change of the physiological sign analysis system mentioned above are within the scope of the present disclosure.

The analysis module 220 may be configured for calculating, analyzing, determining, and/or processing the physiological information. The analysis module 220 may be centralized or distributed. The analysis module 220 may be local or remote. The calculation method may be a particular calculation or a yes/no determination based on a threshold. The analysis process may be real-time or non-real time. The calculation process may be performed by the system or an external computer program. A device used during the calculation process may be an internal or external computing device. The processing may be carried out in real time or not. The processing may be performed by the system or an external device connected to the system.

The output module 230 may be configured for outputting the calculated, analyzed, determined, and/or processed physiological information. The output information may be analog or digital. The output information may be a logic determination result or processed physiological information. The output process may be carried out in real time or not. The output process may be performed by the system or the external device connected to the system. The external device 240 may refer to various devices that directly or indirectly connected to one or more modules of the physiological sign analysis system 110. The external device 240 may be local or remote. The external device 240 may be wired or wireless. For example, the external device 240 may include a LED or LCD screen for displaying the physiological information, or a storage device (e.g., a hard disk, a floppy disk, etc.) for storing the physiological information. The power supply 250 may refer to various devices that may be used for providing power. The power supply 250 may be wired or wireless. The types of the power supply described below are part of practical embodiments and not include all embodiments that can be applied to the system. The power supply may include, without limitations to, an external power supply, an internal battery, or a built-in power generation device of the system. The external alternating current power supply may include but not limited to a household or an industrial alternating current power supply. Further, different countries or regions may have different requirements for the voltage and frequency of the household alternating current, such as but not limited to: 120V and 60 Hz in the United States and Canada, 220V~240V and 50 Hz in most of the European countries, 230V or 240V and 50 Hz in Australia and New Zealand, 220V and 50 Hz in Argentina and Chile, 110V or 220V and 60 Hz in Brazil, 220V and 50 Hz in most areas of Egypt, South Africa, and Morocco, 127V or 220V and 60 Hz in Saudi Arabia, 230V and 50 Hz in Turkey, 100V and 50 Hz (east) or 60 Hz (west) in Japan, 220V and 50 Hz in Mainland China, the Hong Kong Special Administrative Region, and the Macao Special Administrative Region, 220V and 60 Hz in South Korea, and 110V and 60 Hz in China Taiwan. Further, the system may be connected to the household alternating current through an internal wire or through a standard plug. The wire connection between the system and the household alternating current may refer to but not limited to the following standards: United States standards UL 244A, UL514A, UL514B, UL514C, UL514D, CSA C22.2 No. 177, NFPA70, etc., European Standards IEC/EN 61058-1, IEC/EN 61347-2-11, IEC/EN 61347-1, etc., Australian standards AS/NZS3123, AS/NZS3131, AS/NZS60320.1 AS/NZS60320.2.2, etc., Japanese standards JIS C 8281-2-1, etc., and Chinese standards GB16915.1, GB16915.2, GB16915.3, EN60669, etc. The voltage, frequency, and household power supply standards listed above are only provided for illustration purposes, and other types of voltage, frequency, and household power supply standards may also be applied to the system. For example, a power supply may be wirelessly connected to the system, for example, energy may be transmitted from the power supply to the information acquisition system through inductive coupling. The technique may also transmit energy to the battery for operations of the information acquisition system.

The physiological sign analysis system may also use a battery (also be referred to as "a storage battery") as a power supply. The battery may include but not limited to a disposable battery, and also may be a rechargeable battery. The type of the battery may include but not limited to a lead-acid battery, a nickel-cadmium battery, a nickel-metal hydride battery, a lithium ion battery, a fuel cell, a zinc-manganese battery, an alkaline manganese battery, a lithium battery, a mercury battery, and a zinc-mercury battery. The type of the battery may also be any other type. If a rechargeable battery is used, the battery may be charged by an interface of the physiological sign extraction system. The battery may be taken out to be charged or the battery may be charged using a wireless charging technology.

The cloud server 260 may be used to store data associated with the operation of the physiological sign analysis system and may provide data call support for modules in the system in real-time or in non-real time. The cloud server 260 may be used as a cloud database of the physiological sign analysis system.

The analysis module 220 may be connected to the acquisition module 210 through a wired or a wireless connection. The acquisition module 210 and the analysis module 220 may be connected to the output module 230 through a wired or a wireless connection. The acquisition module 210, the analysis module 220, and the output module 230 may be connected to different power supplies respectively, or two or three of the three modules may share a common power supply. The acquisition module 210, the analysis module 220, and the output module 230 may be connected to external devices respectively. The external device may be connected to one or more modules of the system. The connection among the modules or the external device may be wired or wireless. The engine 200 may be connected to the cloud server 260 and the connection may be wired or wireless. The modules and devices described above are unnecessary, for persons having ordinary skills in the art, after understanding the principle of the present disclosure, may make multiple modifications and variations in the form and details of the system without departing the principle and structure of the present disclosure. The modules may be combined randomly, part of the modules may be deleted, or new modules may be added. However, those modifications and variations are within the scope of the present disclosure. For example, the acquisition module 210 and the output module 230 may be combined as an independent module, which may be used for acquiring and outputting the physiological information. The independent module may be connected to the analysis module 220 via a wired or a wireless connection. The modules described above may include an integrated storage device that may be used for temporary storage or long-term storage. The engine 200 may include an independent storage module that may be used for storing the acquired, and/or calculated, analyzed, processed physiological information. Those modifications and variations are within in the scope of the present disclosure.

Connections among the modules of the physiological sign analysis system, connections among the modules and the external device, and connections among the system and the storage device or the cloud server are not limited to the above description. The connections mentioned above may be used independently or may be combined with each other. The modules may be integrated in an independent module that may be used to perform operations of the modules. The external device may be integrated in the implement devices of one or more modules, or one or more modules may be integrated in one or more external devices. The connections among the modules of the physiological sign analysis system, the connections among the modules and the external device, and the connections among the system and the storage device or the cloud server may be wired or wireless. The wired connection may include, without limitations to, electric wire, optical fiber, etc. The wireless connection may include, without limitations to, Bluetooth, infrared connection, radio communication, etc.

Figure 3:
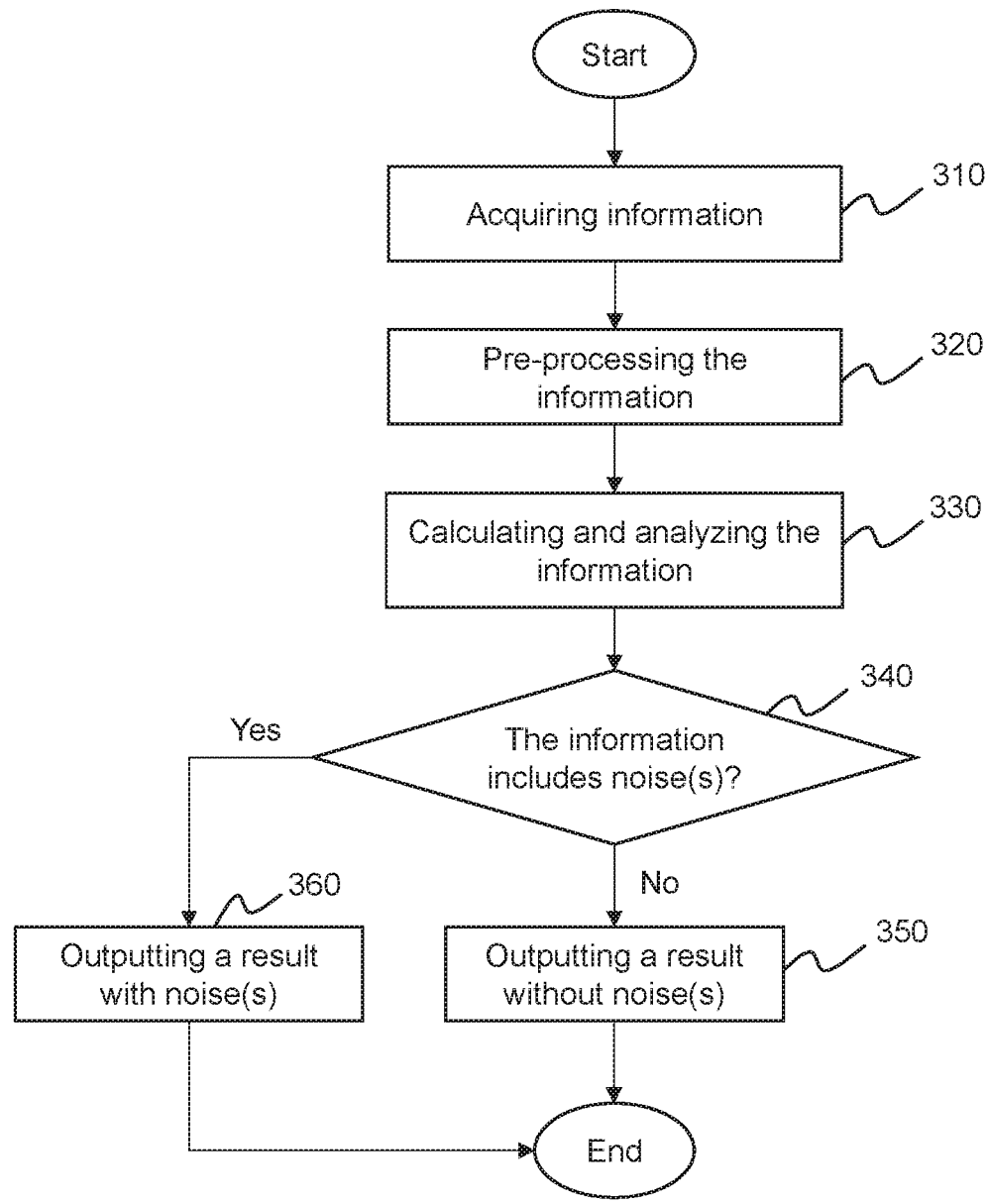
FIG. 3 is a flowchart illustrating an operation process of the system.

FIG. 3 is a flowchart of an exemplary process of the physiological sign analysis system. The process may include steps below: in step 310, the physiological information may be acquired. The acquired information may be further stored in the acquisition module 210 (see FIG. 2), any available storage device (not shown), or the cloud server 260. It should be noted that the acquired information may be not stored in any of the storages and may be transmitted directly for further process. In step 320, the acquired information may be pre-processed. The pre-process may be performed by the analysis module 220, or an independent preprocess module (not shown). The acquired information may be optimized through the pre-process. The pre-process procedure may include, without limitations to, amending, changing, or eliminating partial noise information or redundant information. Methods used during the pre-process may include, without limitations to, low pass filtering, band pass filtering, median filtering, morphological filtering, wavelet transform, curve fitting, etc. After the pre-process step, obvious noises (e.g., baseline drift noise) may be removed from the physiological information. Then the process may proceed to step 330 for further calculation or analysis. The calculation or analysis may be performed by the analysis module 220 and the physiological information may be calculated or analyzed through a plurality of built-in algorithms in the analysis module 220. After the calculation or analysis, the process may proceed to step 340. In step 340, whether the physiological information includes noise or not may be determined. If the answer is "NO", the process may proceed to step 350 to output a noise determination result that there is no noise. If the answer is "YES", the process may proceed to step 360 to output the noise determination result that noises occur in the physiological information. The methods and steps may be performed in any suitable order or may be performed simultaneously. Additionally, any independent step may be deleted without departing the subject and the scope. Various aspects of the embodiments described above may be combined with various aspects of other embodiments to form a further embodiment without missing an intended effect. For example, the pre-process step 320 may be unnecessary, or one or more optional steps may be added between the pre-process step and the analysis step, for example, a step in which the pre-process result may be backed up, or a step in which a result generated in any step may be backed up.

Figure 4:
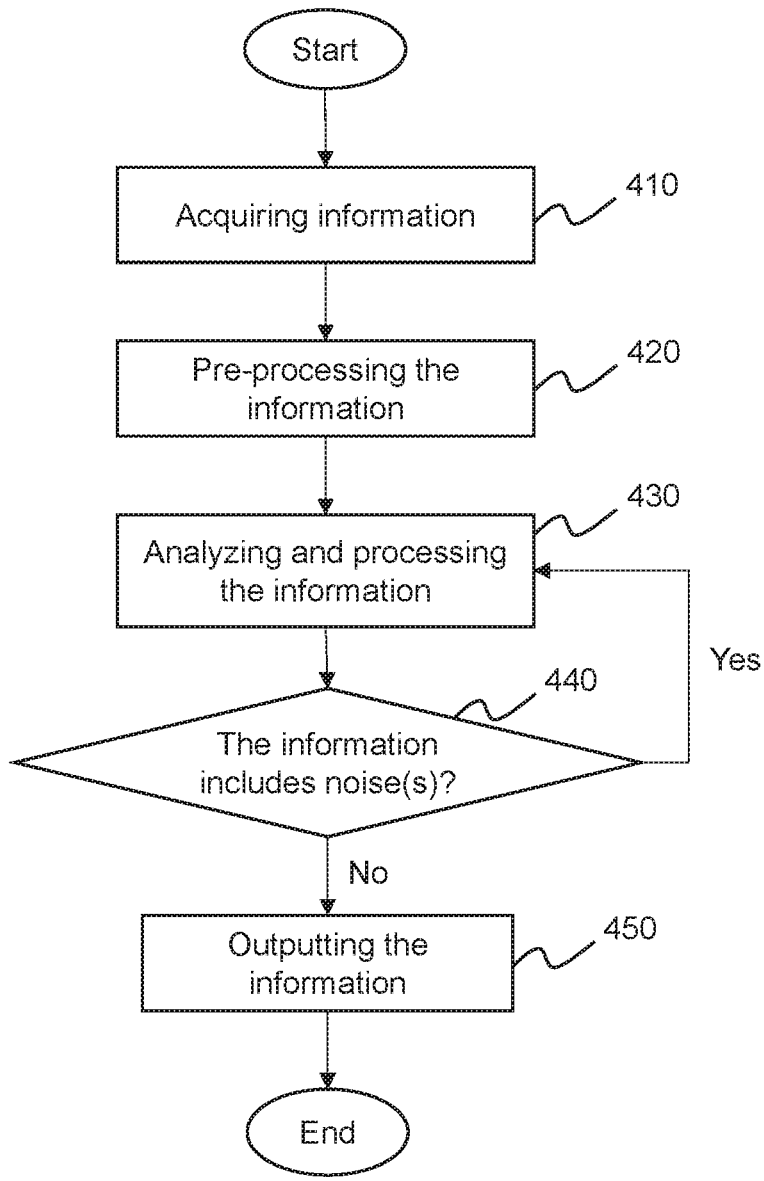
FIG. 4 is another flowchart illustrating another operation process of the system.

FIG. 4 is another flowchart of an exemplary process of the physiological sign analysis system. The process may include steps below: in step 410, the physiological information may be acquired. The acquired information may be further stored in the acquisition module 210 (see FIG. 2), any available storage device (not shown), or the cloud server 260. It should be noted that the acquired information may be not stored in any of the storages and may be transmitted directly for further process. In step 420, the acquired information may be pre-processed. The pre-process may be performed by the analysis module 220, or an independent preprocess module (not shown). The acquired information may be optimized through the pre-process. The pre-process procedure may include, without limitations to, amending, changing or eliminating partial noise or redundant information. Methods used during the pre-process step may include, without limitations to, low pass filtering, band pass filtering, median filtering, morphological filtering, wavelet transform, curve fitting, etc. After the pre-process step, obvious noises (e.g., baseline drift noise) may be removed from the physiological information. Then the process may proceed to step 430 for further calculation or analysis. The calculation or analysis may be performed by the analysis module 220 and the physiological information may be calculated or analyzed through a plurality of built-in algorithms in the analysis module 220. After the calculation or analysis, the process may proceed to step 440. In step 440, whether the physiological information includes noise or not may be determined. If the answer is "NO", the process may proceed to step 350 to output a noise determination result that there is no noise. If the answer is "YES", the process may return back to step 430 to process the physiological information. The physiological information may be analyzed and processed to remove noise. In step 450, the physiological information with noise(s) removed may be output. The output process may be performed by the output module 230. The methods and steps may be performed in any suitable order or may be performed simultaneously. Additionally, any independent step may be deleted without departing the subject and the scope. Various aspects of the embodiments described above may be combined with various aspects of other embodiments to form a further embodiment without missing an intended effect. For example, the noises may be processed or removed in step 430 in real time, or the physiological information may be stored in any storage device (not shown) or the cloud server 260 and the physiological information may be loaded by the analysis module 220 in non-real time to be further processed.

Figure 5:
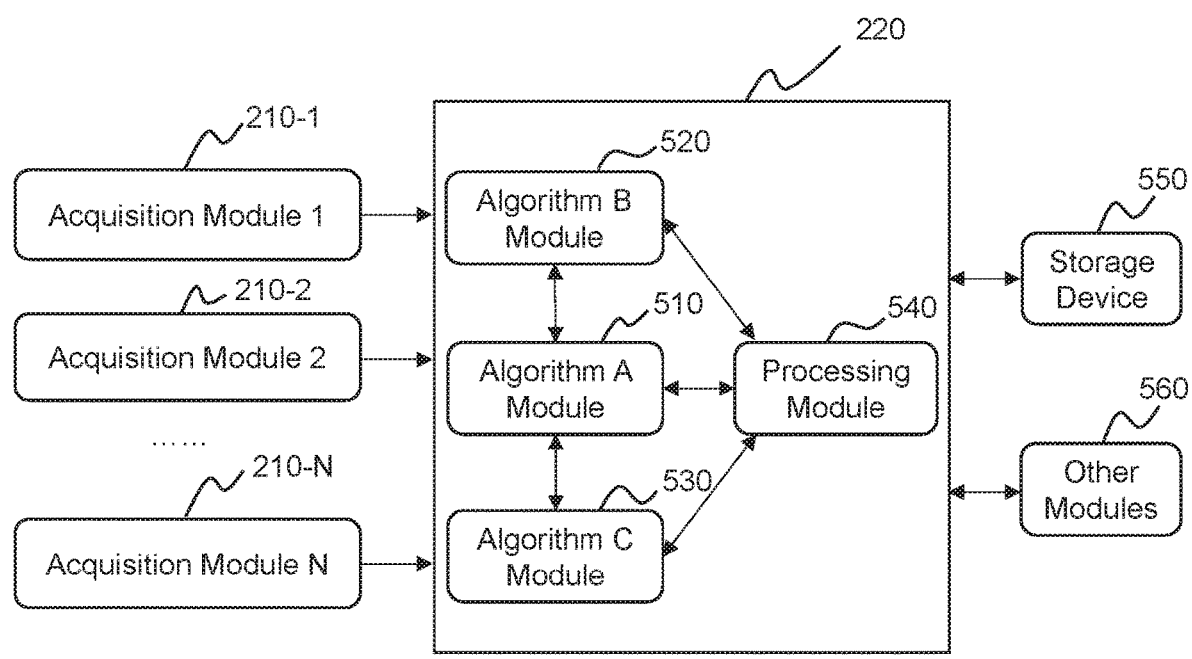
FIG. 5 is a schematic diagram illustrating an analysis module.

FIG. 5 is an exemplary schematic diagram of the analysis module 220 and surrounding devices. The analysis module 220 may include an algorithm A module 510, an algorithm B module 520, an algorithm C module 530, and a processing module 540. The analysis module 220 may be connected to the storage device 550 and other modules 560. The storage device 550 may be an independent device, or may be integrated in the analysis module 220 or the acquisition module 210. The analysis module 220 may be selectively connected to one or more information acquisition modules including, 210-1, 210-2, . . . , 210-N. The analysis module 220 may be selectively connected to other modules. The connection among the modules or devices may be wired or wireless. The algorithm A module 510, the algorithm B module 520, the algorithm C module 530, and the processing module 540 may be connected to each other, or may be connected to other modules independently, the connection is not limited to that illustrated in FIG. 5. The descriptions of the analysis module are only provided for illustration purposes, and should be not be considered as the only practical embodiment.

Each of the modules may be implemented via one or more components and the function of each module is not limited to thereof. For persons having ordinary skills in the art, after understanding the principle of the analysis and processing and without departing the principle, may make multiple modifications and variations in the form and details of the practice and steps of the analysis module, further make simple extrapolations and replacements, and modify or combine the order of the modules without further efforts. However, those modifications and variations are within the scope of the present disclosure. For example, the analysis module 220 may be configured to perform different functions, including, determining whether noises occur in the acquired physiological information, or removing the noises in the physiological information, or both. If in the case that the analysis module 220 is only configured to determine whether noises occur, the processing module 540 may be unnecessary. Similarly, the three algorithm modules may be co-existed, or existed independently. When the analysis module 220 operates, one or more algorithm modules may be selected to be operated, or the algorithm modules may be operated in a certain order, or the algorithm modules may be operated simultaneously or at a certain time interval. Further, the results generated by any algorithm module may be further processed by other algorithm modules, or the results generated by the algorithm modules may be transmitted to the processing module 540 simultaneously or not to be further processed.

The acquired, calculated, analyzed, determined, and/or processed physiological information by the analysis module 220 may be selectively stored in the storage device 550 to be further loaded or analyzed by the analysis module 220 in any time. The storage device 550 may be any medium that may be used to read and/or write information, including but not limited to, a random access memory (RAM) and a read only memory (ROM), particularly for example, a disk, a floppy disk, a flash disk, a light disk, etc. Exemplary RAM may include but not limited to a decimal counter, a selector, a delay line storage, a Williams tube, a dynamic RAM (DRAM), a static RAM (SRAM), a thyristor RAM (T-RAM), and a zero-capacitor RAM (Z-RAM), etc. Exemplary ROM may include but not limited to a magnetic bubble memory, a magnetic button line memory, a thin film memory, a magnetic thin film plating line memory, a magnetic core memory, a magnetic drum memory, a CD-ROM drive, a hard disk, a tape, an early NVRAM (non-volatile memory), a phase change memory, a magnetic resistance random memory, a ferroelectric random memory, a nonvolatile SRAM, a flash memory, an electronic erase type of rewritable read-only memory, an erasable programmable read-only memory, a programmable read-only memory, a mask ROM, a floating gate connected random access memory, a nano-random variable resistance memory, a racetrack memory, a resistive random-access memory, a programmable metallization cell, etc. The storage devices mentioned above are provided for illustration purposes, and the storage device for the system is not limited to those.

Figure 6:
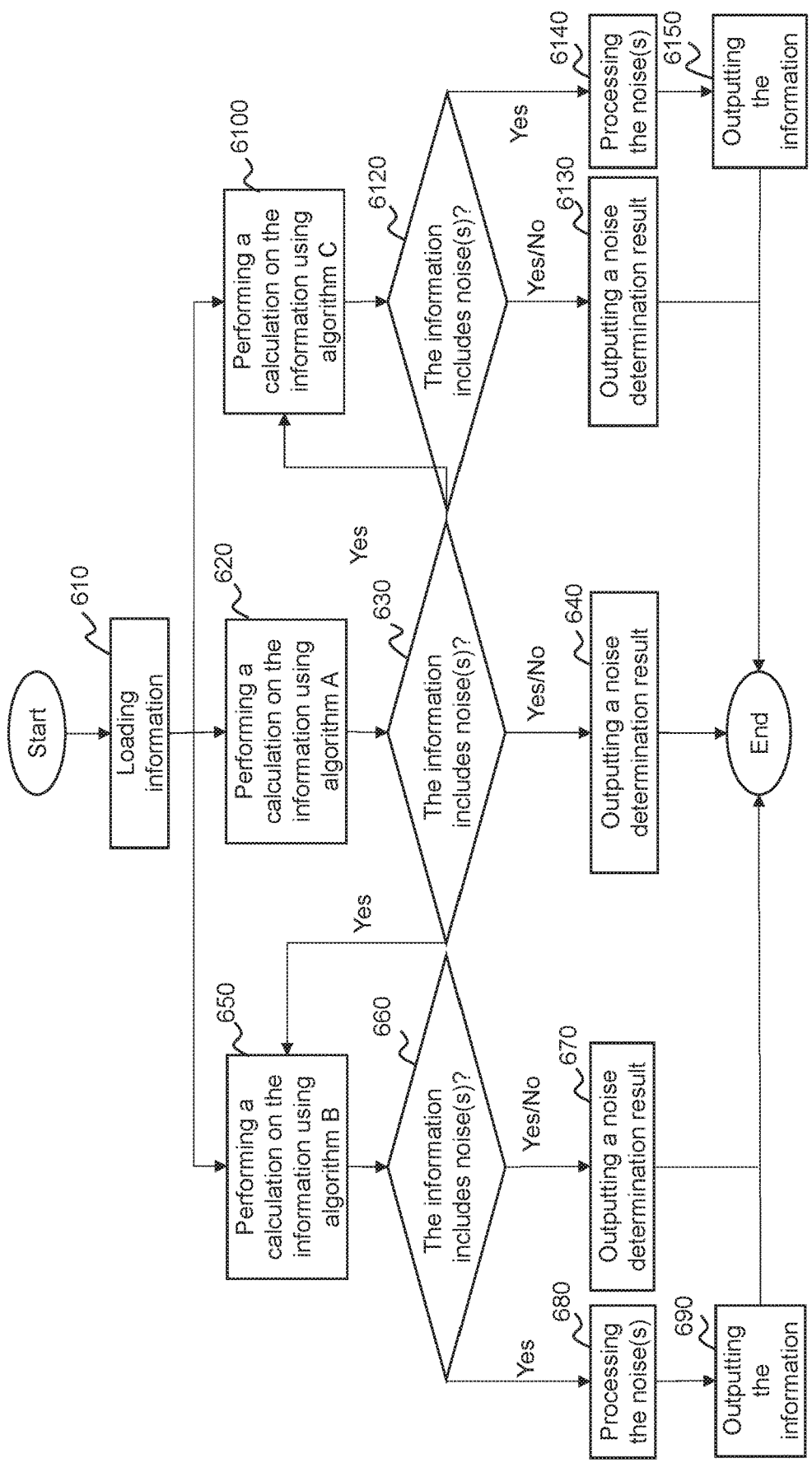
FIG. 6 is a flowchart illustrating an analysis process performed by the analysis module.

FIG. 6 is a flowchart illustrating a process for performing a calculation, an analysis, a determination, a processing by the analysis module 220. In step 610, the physiological information of the subject may be loaded, and then the process may proceed to a calculation step 620, 650, or 6100. The calculation steps may be unnecessary, the process may select one or more calculation steps to perform. The calculation steps may be performed independently, or in a certain order, or simultaneously. Take performing A-algorithm first for example, the process may proceed to step 620 to calculate the physiological information and generate a calculation result. The calculation result may be determined and a determination result may be generated in step 630. If the determination result indicates that there is no noise in the physiological information, then a noise result that there is no noise may be outputted and the analysis process may end. If the determination result indicates that the physiological information includes noise(s), then a noise result that the physiological information includes noise(s) may be outputted and the analysis process may end. In this situation, the process may also proceed to step 650 or step 6100 to further calculate or analyze the physiological information. Take proceeding to step 650 for example, in step 650, the physiological information may be calculated or analyzed and a calculation or analysis result may be generated. The calculation or analysis result may be transmitted to step 660 to determine whether the physiological information includes noise. If it is determined that the physiological information includes noise(s), the noise(s) may be processed and removed in step 680. The physiological information with noise(s) removed may be outputted in step 690 and the whole process may end. Similarly, after the physiological information is loaded in step 610, the process may proceed to step 650 to calculate or analyze the physiological information and generate a calculation result. Then the calculation result may be transmitted to step 660 to be determined. If it is determined that there is no noise, a noise result that there is no noise may be outputted in step 670 and the whole process may end. The output process may be performed by the output module 230. If it is determined that the physiological information includes noise(s), a noise result that the physiological information includes noise(s) may be outputted in step 670 and the whole process may end. In this situation, the process may also proceed to step 680 to remove the noise(s). The physiological information with noise(s) removed may be outputted in step 690 and the whole process may end. Similarly, after the physiological information is loaded in step 610, the process may proceed to step 6100 to calculate or analyze the physiological information and generate a calculation result. Then the calculation result may be transmitted to step 6120 to be determined. If it is determined that there is no noise in the physiological information, a noise result that there is no noise may be outputted in step 670 and the whole process may end. The output process may be performed by the output module 230. If it is determined that the physiological information includes noise(s), a noise result that the physiological information includes noise(s) may be outputted in step 670 and the whole process may end. In this situation, the process may also proceed to step 6140 to remove the noise(s). The physiological information with noise(s) removed may be outputted in step 6150 and the whole process may end. The descriptions of the analysis and processing of the physiological information above are only provided for illustration purposes, and should be not be considered as the only practical embodiment. For persons having ordinary skills in the art, after understanding the principle of the algorithms, may make multiple modifications and variations in the form and details of the practice and steps of the analysis and processing of the information without departing the principle. However, those modifications and variations are within the scope of the present disclosure. For example, when the analysis module 220 is configured for noise detecting, and in this case steps 680 and 6140 may be unnecessary. During the calculation process using the B-algorithm, data generated during the calculation process using the C-algorithm may be used. Similarly during the calculation process using the C-algorithm, data generated during the calculation process using the B algorithm may be used. The calculation results using the A, B, and C algorithm may be cycle used.

The A-algorithm, B-algorithm, and C-algorithm may be used to calculate or process different features in the physiological information, or may be used to calculate or process the same feature in different ways. The positions of steps 620, 650, and 6100 in the flowchart may be changed with each other, and the order of the three algorithms may be randomly combined.

For example, the loaded physiological information may be calculated or analyzed using the B-algorithm and a calculation result may be generated. A determination result that whether the physiological information includes noise(s) may be generated based on the calculation result and the determination result may be further calculated or determined using the A-algorithm or the C-algorithm. In a particular embodiment, during the calculation process using the A-algorithm, a waveform of the physiological information may be extracted, and the physiological information may be calculated or analyzed based on the extracted waveform to determine whether the physiological information includes noise(s). If the determination result indicates that there is no noise, then the noise determination result may be outputted by the output module 230, and the whole analysis process may end; if the determination result indicates that the physiological information includes noise(s), then the noise(s) may be further recognized using the B-algorithm or the C-algorithm, or the noise determination result may be outputted directly by the output module 230. During the calculation process using the B-algorithm, the features in the waveform may be calculated or analyzed, and the features may be marked. One or more threshold values may be set and the noise(s) may be recognized based on a comparison of the features with the threshold values. After the calculation process using the B-algorithm, the noise(s) may be determined and recognized, then the noise(s) may be processed and removed by the processing module 540. The physiological information with noise(s) removed may be outputted by the output module 230, or the noise determination result may be outputted directly by the output module 230. During the calculation process using the C-algorithm, an eigenvalue of the physiological information may be obtained. An eigenvalue threshold may be set and whether the physiological information includes noise(s) may be determined based on the eigenvalue threshold. For example, an F-IMF value of the physiological information may be obtained by an EMD calculation process. A mean value and a variance value may be calculated through a normalization process. A mean value threshold and a variance value threshold may be set and whether the physiological information includes noise(s) may be determined. The noise determination result may be outputted by the output module 230.

The descriptions mentioned above regarding the three algorithms are only provided for illustration purposes, and should be not be considered as the only practical embodiment. For persons having ordinary skills in the art, after understanding the principle of the algorithms, may make multiple extensions or evolutions in the three algorithms, delete step(s), add step(s), or make combinations of the steps to obtain better calculation or analysis effect.

Figure 7:
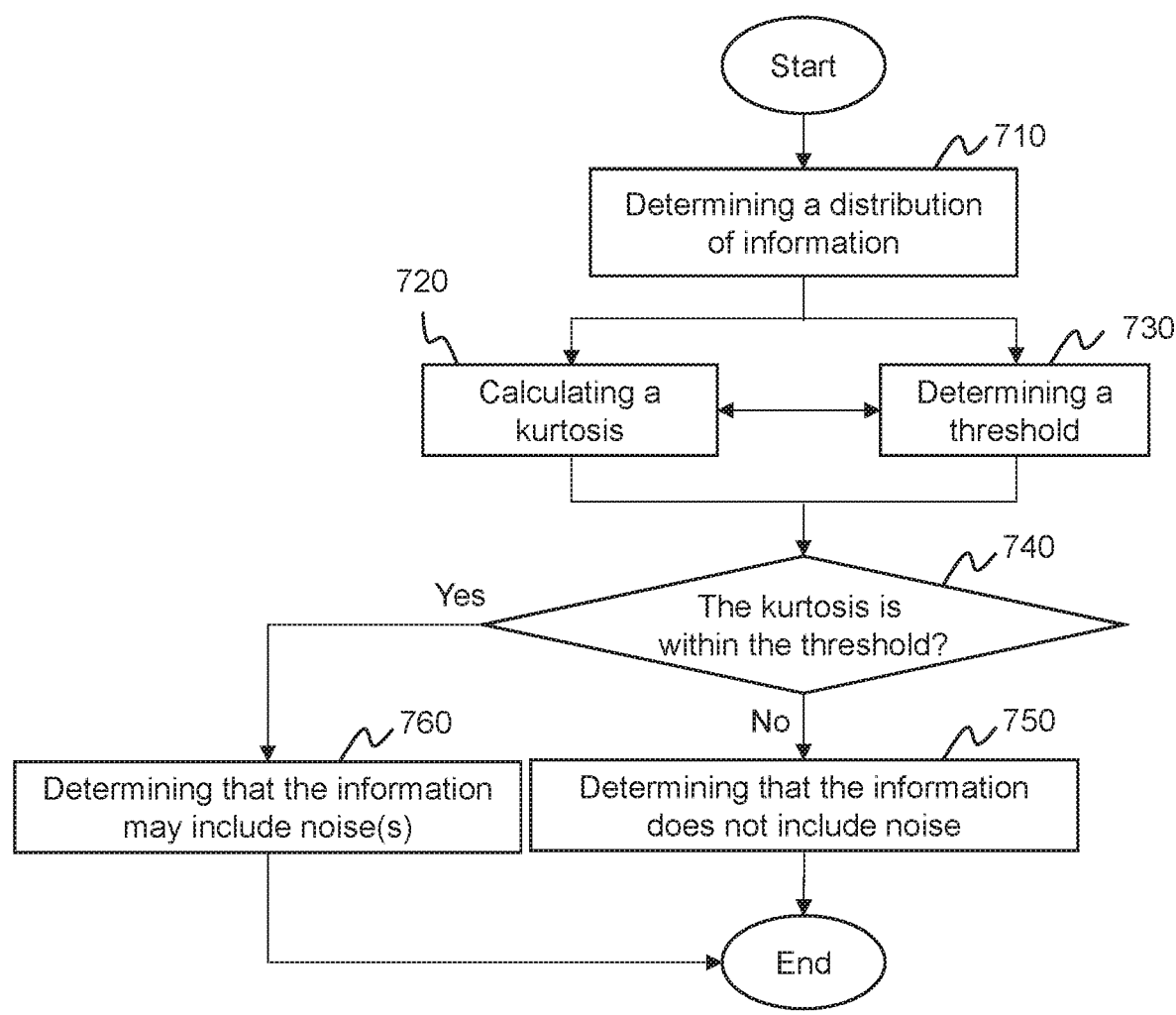
FIG. 7 is a flowchart illustrating a process for analyzing physiological sign based on A-algorithm in the present disclosure.

FIG. 7 is a flowchart illustrating an analysis process using A-algorithm. In step 710, statistical magnitude information of the physiological information may be determined. As used herein, the statistical magnitude may include but not limited to a wave width of the physiological information, a kurtosis of the physiological information, an interval (an interval between waves) of the physiological information, a wave slope (including but not limited to a statistical parameter (e.g., a maximum value, a minimum value, an average value of the slope)) of the physiological information, a wave amplitude of the physiological information, a wave frequency of the physiological information, a coefficient associated with the waves of the physiological information, a wave rise time of the physiological information, a wave fall time of the physiological information, a wave area of the physiological information, a ratio of the wave area to the wave width of the physiological information, a moment calculation (e.g., a secondary moment, a third moment, a fourth moment, a higher moment) of the physiological information, etc. After step 710, step 720 and step 730 may be performed simultaneously. In step 720, the kurtosis of the physiological information may be calculated. Simultaneously in step 730, a threshold may be set according to the distribution of the physiological information. In step 740, the calculated kurtosis may be compared with the threshold. If the kurtosis exceeds the scope of the threshold, it may indicate that there is no noise in the physiological information as shown in step 750, and then the analysis process may end; if the kurtosis is within the scope of the threshold, it may indicate that the physiological information includes noise(s) as shown in step 760, and then the analysis process may end. The descriptions of the A-algorithm above are only provided for illustration purposes, and should be not be considered as the only practical embodiment. For persons having ordinary skills in the art, after understanding the principle of kurtosis calculation and noise determination, may make multiple modifications and variations in the form and details of the practical embodiments and steps of the A-algorithm. However, those modifications and variations are within the scope of the present disclosure. For example, step 710 may be omitted and the whole process may start from step 720 to calculate the kurtosis of the physiological information. Various methods or manners may be used during the calculation process, for example, direct calculation, simulation, etc. After ending the process of the A-algorithm, the whole process may end or the process may proceed to a process for further analysis or calculation performed by the algorithm B module 520 or the algorithm C module 530. Similarly, the process of the A algorithm, the process of the B-algorithm, and the process of the C-algorithm may be performed simultaneously.

Figure 8:
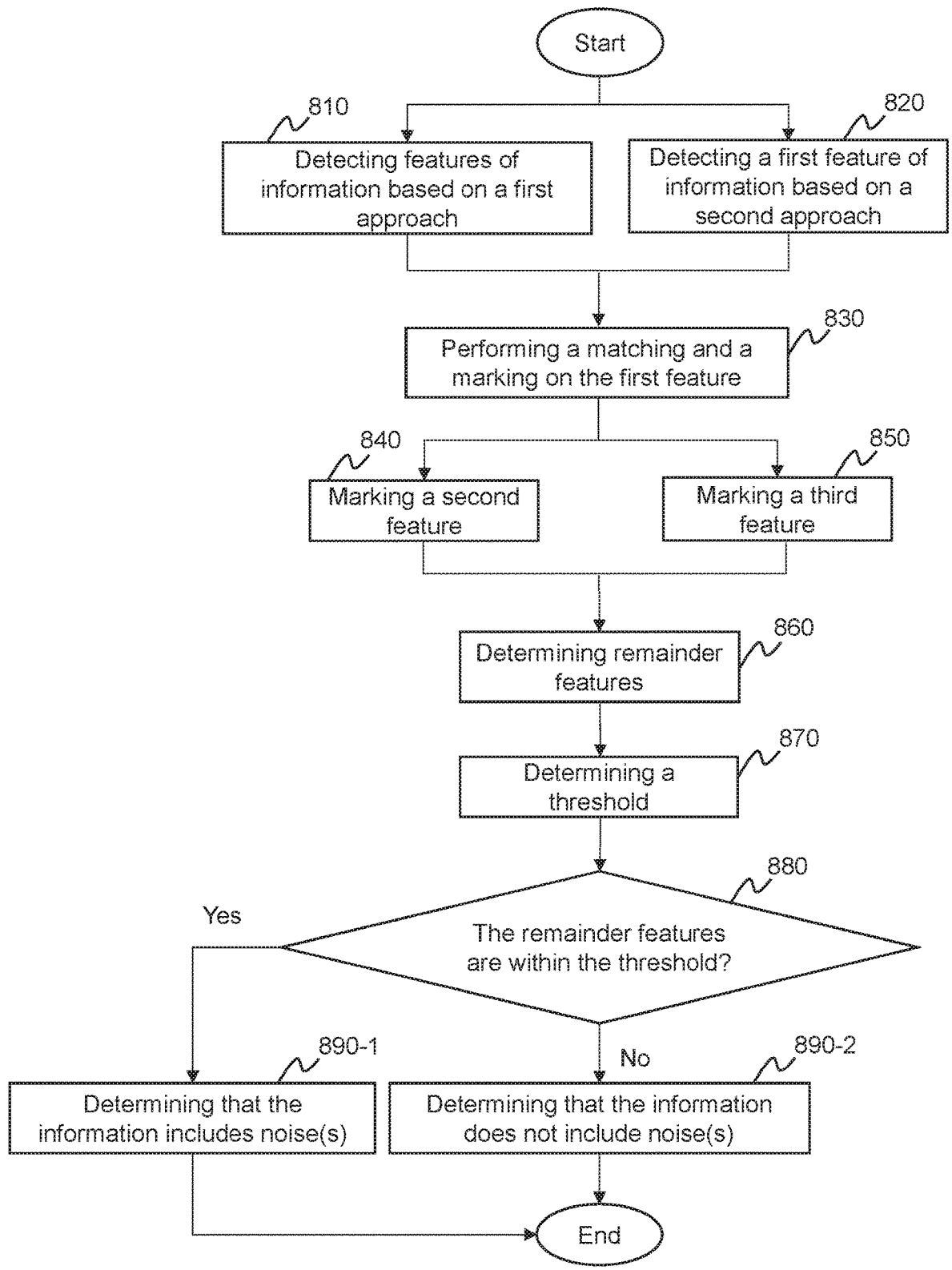
FIG. 8 is a flowchart illustrating a process for analyzing physiological sign based on B-algorithm in the present disclosure.

FIG. 8 is a flowchart illustrating an analysis process using B-algorithm. At the beginning, steps 810 and 820 may be performed respectively. In step 810, features of the physiological information may be detected based on a first approach and the detected all feature results may be stored. In step 820, a first feature of the physiological information may be detected based on a second approach and the detected first feature may be stored, wherein the second approach may be different from the first approach. Afterwards, in step 830, a matching may be performed between the all feature results detected in step 810 and the first feature detected in step 820. A position of the first feature in the all feature results may be marked. It should be noted that during the matching, a threshold may be set. During the matching, if the matching is within the threshold range, it indicates that the matching is completed. According to the first feature marked in step 830, a second feature and a third feature may be marked respectively in step 840 and step 850. Similarly, during the marking process of the second feature and the third feature, thresholds may be set. During the marking process, if the marking is within the threshold range, it indicates that the marking process is completed. According to the marked first feature, the marked second feature, and the marked third feature, remainder features of the physiological information may be determined in step 860. Then a threshold may be set in step 870, and the remainder features of physiological information may be compared with the threshold one by one in step 880. If the comparison result is within the scope of the threshold, it indicates that the physiological information includes noise(s) as shown in step 890-1, and the calculation or analysis process may end; if the comparison result is not within the scope of the threshold, it indicates that there is no noise in the physiological information as shown in step 890-2, and the calculation or analysis process may end. The descriptions of the B-algorithm above are only provided for illustration purposes, and should be not be considered as the only practical embodiment. For persons having ordinary skills in the art, after understanding the principle of kurtosis calculation and noise determination, may make multiple modifications and variations in the form and details of the practical embodiments and steps of the A-algorithm. However, those modifications and variations are within the scope of the present disclosure. For example, in step 810, the feature detection may be performed on the complete physiological information or a part of the physiological information within a time interval. Similarly, the part of the physiological information within which the first feature may be detected in step 820 may correspond to that in step 810. In step 840 and step 850, the second feature and the third feature may be marked within a time interval before or after the position of the first feature, and wherein the time interval may be adjusted as required. Additionally, step 840 and step 850 may be unnecessary and may be deleted or added according to operations of the algorithm process.

Figure 9:
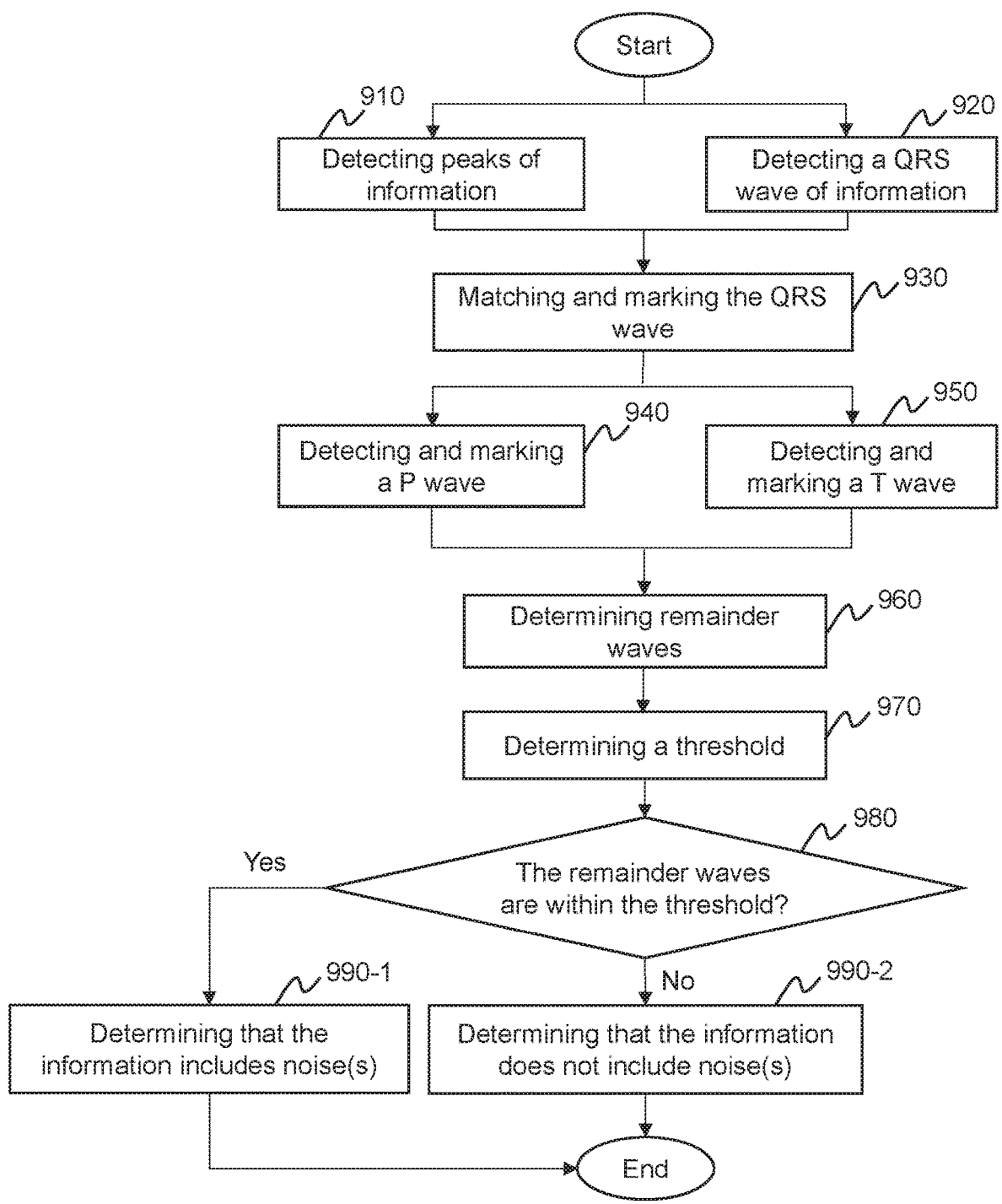
FIG. 9 is a another flowchart illustrating a process for analyzing physiological sign based on B-algorithm in the present disclosure.

FIG. 9 is a flowchart illustrating another analysis process using B-algorithm. At the beginning, a peak detection and a QRS wave detection may be performed on the physiological information respectively in step 910 and step 920. In step 910, the peak detection may include steps below: absolute values of the physiological information may be calculated to obtain all peak results and a threshold may be set. If a value of a peak satisfies the threshold condition, the peak may be reserved, otherwise the peak may be abandoned. The above steps may be repeated and the all peak results may be obtained. In step 920, methods that may be used for the QRS wave detection may include, without limitations to, an entropy calculation, a difference method, a band-pass filter method, a morphological algorithm, a length and energy transformation method, an artificial neural network, a genetic algorithm, a sentence analysis, a matched filtering method, a Hilbert transform, an ECG template method, a zero crossing detection, a threshold method, a template matching method, a wavelet transform method, neural network method, or the like, or a combination thereof. The QRS detection result may include but not limited to a wave width of a QRS wave, a RR interval (an interval between QRS waves), a slope of the QRS wave (including but not limited to a statistical parameter (e.g., a maximum value, a minimum value, an average value of the slope), an amplitude of the QRS wave, a parameter associated with the QRS wave, a rise time of the QRS wave, a fall time of the QRS wave, an area of the QRS wave, a ratio of the area to the width of the QRS wave, etc. Afterwards, in step 930, a matching may be performed between the peak results detected in step 910 and the QRS wave detected in step 920, and a peak matched with the QRS wave may be marked as a QRS wave. It should be noted that a threshold may be set during the matching process, and only when the value of the peak is within the scope of the threshold, it indicates that the peak is matched with the QRS wave. According to the position of the marked QRS wave, a P wave and a T wave may be detected respectively as shown in step 940 and step 950. Similarly, thresholds may be set for the P wave detection and T wave detection, and only when the value of the peak is within the scope of the threshold, the peak could be marked as a P wave or a T wave. Afterwards, in step 960, the marked QRS wave, P wave, and T wave may be excluded, and the remainder waves may be obtained. In step 970, a threshold may be set. In step 980, whether peak values of the remainder waves are within the scope of the threshold may be determined. If the determination result is within the scope of the threshold, it indicates that the physiological information includes noise(s) as shown in step 990-1, and the calculation or analysis process may end; if the determination result is not within the scope of the threshold, it indicates that there is no noise in the physiological information as shown in step 990-2, and the calculation or analysis process may end. The descriptions of the B-algorithm above are only provided for illustration purposes, and should be not be considered as the only practical embodiment.

Figure 10:
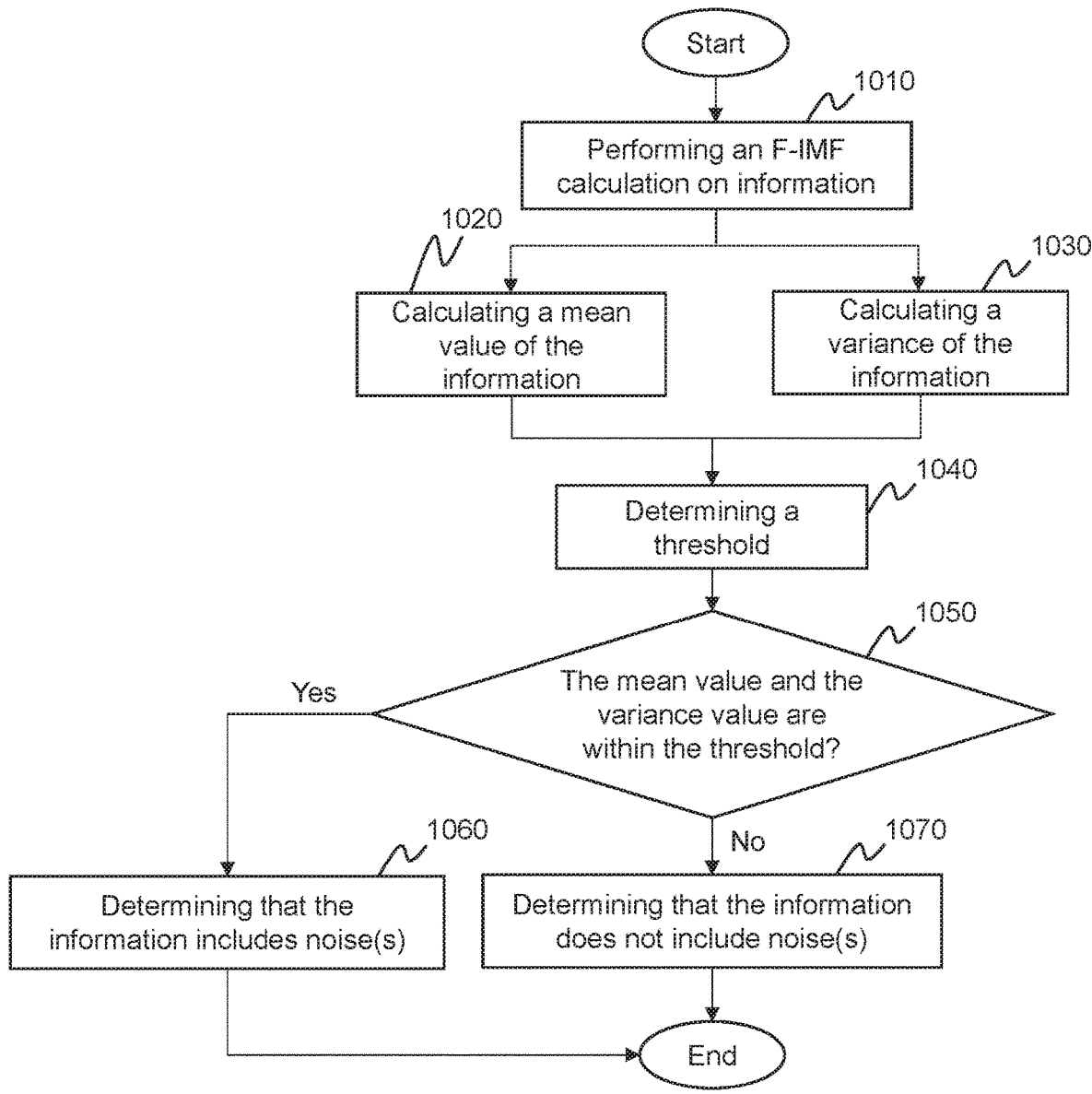
FIG. 10 is a flowchart illustrating a process for analyzing physiological sign based on C-algorithm in the present disclosure.

FIG. 10 is a flowchart illustrating an analysis process using C-algorithm. In step 1010, the physiological information may be calculated based on an EMD algorithm to obtain an F-IMF result. The calculation process may include calculating each IMF of the physiological information, wherein the calculated IMFs may be arranged from high to low according to the frequency. After the F-IMF result of the physiological information is obtained, a square value of the F-IMF result may be calculated and the square value may be normalized. A mean value and a variance value of the normalized data may be further calculated in step 1020 and step 1030 respectively. In step 1040, a mean value threshold and a variance value threshold may be set respectively. Then the process may proceed to step 1050. In step 1050, the calculated mean value and the calculated variance may be compared with the mean value threshold and the variance value threshold. If the comparison result is within the scope of the threshold, it indicates that the physiological information includes noise(s) as shown in step 1060, and the calculation or analysis process may end; if the comparison result is not within the scope of the threshold, it indicates that there is no noise in the physiological information as shown in step 1070, and the calculation or analysis process may end. The descriptions of the C-algorithm above are only provided for illustration purposes, and should be not be considered as the only practical embodiment. For persons having ordinary skills in the art, after understanding the principle of the EMD algorithm, may make multiple modifications and variations in the form and details of the practical embodiments and steps of the C-algorithm. However, those modifications and variations are within the scope of the present disclosure. For example, the calculation using the C-algorithm may be carried out through a real time calculation procedure, or a non-real-time simulation procedure. The F-IMF calculation in step 1010 may be carried out through a computer program, or by calling data from the EMD algorithm database.

The above descriptions are a brief summary of the three algorithms and a brief description of main steps, the three algorithms may be applied independently, or may be applied in a form of combinations. Under appropriate circumstances, the steps of the three algorithms may be executed independently in a proper order, or simultaneously. Additionally, one or more steps of any of the algorithms may be deleted without deviating the subject and scope of the present disclosure. For persons having ordinary skills in the art, after understanding the principle and the main steps of the three algorithms, may add steps or delete steps to obtain a better calculation or analysis effect without departing the principle. Various aspects of the embodiments described above may be combined with various aspects of other embodiments to form a further embodiment without missing an intended effect.

EXAMPLES

Example 1

The power supply may be switched on and the acquisition module 210 may be initiated. After initialization and environment self-adaptation, the module may collect ECG information of a subject. The collected ECG information may include wave shape, time interval, frequency, phase, peak, valley, amplitude, etc. The acquired information may be stored in an internal storage device of the module, an independent storage module (not shown), or the cloud server 260. Afterwards, the analysis module 220 may read the ECG information from the storage device or the storage module, and pre-process the information to eliminate obvious noise(s) from the information through filtering. The preprocessed ECG information may be transmitted to the algorithm A module 510. The algorithm A module 510 may determine a distribution type of the information, calculate a kurtosis of the information by using a built-in A algorithm, and generate a kurtosis calculation result. Then a noise threshold may be set according to the distribution type of the information. If the kurtosis calculation result is larger than the threshold value, it may indicate that there is no noise in the information, and a noise result that there is no noise in the information may be output by the output module 230. If the kurtosis calculation result is smaller than the threshold value, it may indicate that the information includes noise(s), and the noise(s) may be further recognized and removed. Then the information may be transmitted to the algorithm B module 520. The information may be calculated, analyzed, determined, and recognized using a built-in B-algorithm. First, a peak detection may be performed on the information. The peak detection may include but not limited to: calculating an absolute value of the information, detecting a local maximum value, obtaining a preliminary all peak results, setting a historical threshold, and determining whether the preliminary all peak results are within the scope of the historical threshold or not. If a peak result is larger than the historical threshold, the peak may be reserved; if a peak result is smaller than the historical threshold, the peak may be abandoned. Then all peak results of the information may be obtained. Simultaneously a QRS wave detection may be performed. The methods for the QRS wave detection may include but not limited to an entropy calculation, a difference method, a band-pass filter method, a morphological algorithm, a length and energy transformation method, an artificial neural network, a genetic algorithm, a sentence analysis, a matched filtering method, a Hilbert transform, an ECG template method, a zero crossing detection, a threshold method, a template matching method, a wavelet transform method, neural network method, or the like, or a combination thereof. Then a QRS wave detection result may be obtained. The all peak results obtained previously may be matched with the QRS wave detection result. A threshold may be set during the matching. If a peak is within the scope of the threshold, it may indicate that the peak is matched with the QRS wave and the position of the matched peak may be marked. Then a P wave detection may be carried out sequentially. The peaks within a certain time interval from the position of the marked QRS wave may be extracted for the P wave detection. There is no strict limit for the time interval. For example, the time interval may be set as 300 milliseconds. If only one peak appears within the time interval and an amplitude of the peak is smaller than or equal to that of the QRS wave, the peak may be marked as a P wave. If more than one peaks appear within the time interval, a peak nearest to the QRS wave may be marked as a P wave, provided that an amplitude of the peak is smaller than or equal to that of the QRS wave. The peaks within a certain time interval before the position of the marked QRS wave may be extracted for a T wave detection. Similarly, there is no strict limit for the time interval. For example, the time interval may be set as 400 milliseconds. If only one peak appears within the time interval, and an amplitude of the peak is smaller than or equal to an double value of an amplitude of the QRS wave, the peak may be marked as a T wave. If more than one peaks appear within the time interval, a peak nearest to the QRS wave may be marked as a T wave, provided that an amplitude of the peak is smaller than or equal to the double value of the amplitude of the QRS wave. The remainder peaks excluded the marked QRS wave, the marked P wave, and the marked T wave may be considered as potential noise peaks. A noise ratio may be defined as a ratio of an amplitude of a potential noise peak to an average amplitude of the QRS wave.

The noise threshold condition may be set as follows:

s1: If there is no QRS wave detected or no peak is matched with the QRS wave, it indicates that the information includes noise(s);

s2: If a number of peaks with noise ratios larger than or equal to 1 is larger than a number of QRS waves divided by 2, it indicates that the information includes noise(s);

s3: If a number of peaks with noise ratios larger than or equal to 0.8 is larger than the number of QRS waves multiplied by 0.75, it indicates that the information includes noise(s);

s4: If a number of peaks with noise ratios larger than or equal to 0.5 is larger than the number of QRS waves, it indicates that the information includes noise(s).

A threshold determination may be performed on the potential noise peaks according to the noise threshold condition above. If the peaks do not satisfy the threshold condition, a noise result that there is no noise in the information may be output by the output module 230. If a peak satisfies the threshold condition, the peak may be marked as a noise peak. Similarly, all noise peaks may be marked. Then the marked noise peaks may be transmitted to the processing module 540 for further noise removal. The information with noise(s) removed may be output by the output module 230.

Example 2

The power supply may be switched on and the acquisition module 210 may be initiated. After initialization and environment self-adaptation, the module may collect ECG information of a subject. The collected ECG information may include wave shape, time interval, frequency, phase, peak, valley, amplitude, etc. The acquired information may be stored in an internal storage device of the module, an independent storage module (not shown), or the cloud server 260. Afterwards, the analysis module 220 may read the ECG information from the storage device or the storage module, and pre-process the information to eliminate obvious noise(s) from the information through filtering. The preprocessed ECG information may be transmitted to the algorithm B module 520. The information may be calculated, analyzed, determined, and recognized using a built-in B-algorithm. First, a peak detection may be performed on the information. The peak detection may include but not limited to: calculating an absolute value of the information, detecting a local maximum value, obtaining a preliminary all peak results, setting a historical threshold, and determining whether the preliminary all peak results are within the scope of the historical threshold or not. If a peak result is larger than the historical threshold, the peak may be reserved; if a peak result is smaller than the historical threshold, the peak may be abandoned. Then all peak results of the information may be obtained. Simultaneously a QRS wave detection may be performed. The methods for the QRS wave detection may include but not limited to an entropy calculation, a difference method, a band-pass filter method, a morphological algorithm, a length and energy transformation method, an artificial neural network, a genetic algorithm, a sentence analysis, a matched filtering method, a Hilbert transform, an ECG template method, a zero crossing detection, a threshold method, a template matching method, a wavelet transform method, neural network method, or the like, or a combination thereof. Then a QRS wave detection result may be obtained. The all peak results obtained previously may be matched with the QRS wave detection result. A threshold may be set during the matching. If a peak is within the scope of the threshold, it may indicate that the peak is matched with the QRS wave and the position of the matched peak may be marked. Then a P wave detection may be carried out sequentially. The peaks within a certain time interval from the position of the marked QRS wave may be extracted for the P wave detection. There is no strict limit for the time interval. For example, the time interval may be set as 300 milliseconds. If only one peak appears within the time interval and an amplitude of the peak is smaller than or equal to that of the QRS wave, the peak may be marked as a P wave. If more than one peaks appear within the time interval, a peak nearest to the QRS wave may be marked as a P wave, provided that an amplitude of the peak is smaller than or equal to that of the QRS wave. The peaks within a certain time interval before the position of the marked QRS wave may be extracted for a T wave detection. Similarly, there is no strict limit for the time interval. For example, the time interval may be set as 400 milliseconds. If only one peak appears within the time interval, and an amplitude of the peak is smaller than or equal to an double value of an amplitude of the QRS wave, the peak may be marked as a T wave. If more than one peaks appear within the time interval, a peak nearest to the QRS wave may be marked as a T wave, provided that an amplitude of the peak is smaller than or equal to the double value of the amplitude of the QRS wave. The remainder peaks excluded the marked QRS wave, the marked P wave, and the marked T wave may be considered as potential noise peaks. A noise ratio may be defined as a ratio of an amplitude of a potential noise peak to an average amplitude of the QRS wave.

The noise threshold condition may be set as follows:

s1: If there is no QRS wave detected or no peak is matched with the QRS wave, it indicates that the information includes noise(s);

s2: If a number of peaks with noise ratios larger than or equal to 1 is larger than a number of QRS waves divided by 2, it indicates that the information includes noise(s);

s3: If a number of peaks with noise ratios larger than or equal to 0.8 is larger than the number of QRS waves multiplied by 0.75, it indicates that the information includes noise(s);

s4: If a number of peaks with noise ratios larger than or equal to 0.5 is larger than the number of QRS waves, it indicates that the information includes noise(s).

A threshold determination may be performed on the potential noise peaks according to the noise threshold condition above. If the peaks do not satisfy the threshold condition, a noise result that there is no noise in the information may be output by the output module 230. If a peak satisfies the threshold condition, the peak may be marked as a noise peak. Similarly, all noise peaks may be marked. Then the marked noise peaks may be transmitted to the processing module 540 for further noise removal. The information with noise(s) removed may be output by the output module 230.

Example 3

The power supply may be switched on and the acquisition module 210 may be initiated. After initialization and environment self-adaptation, the module may collect ECG information of a subject. The collected ECG information may include wave shape, time interval, frequency, phase, peak, valley, amplitude, etc. The acquired information may be stored in an internal storage device of the module, an independent storage module (not shown), or the cloud server 260. Afterwards, the analysis module 220 may read the ECG information from the storage device or the storage module, and pre-process the information to eliminate obvious noise(s) from the information through filtering. The preprocessed ECG information may be transmitted to the algorithm A module 510. The algorithm A module 510 may determine a distribution type of the information, calculate a kurtosis of the information by using a built-in A algorithm, and generate a kurtosis calculation result. Then a noise threshold may be set according to the distribution type of the information. If the kurtosis calculation result is larger than the threshold value, it may indicate that there is no noise in the information, and a noise result that there is no noise in the information may be output by the output module 230. If the kurtosis calculation result is smaller than the threshold value, it may indicate that the information includes noise(s), and the noise(s) may be further recognized and removed. Then the information may be transmitted to the algorithm C module 530. The information may be processed by using a built-in C-algorithm including but not limited to an EMD calculation. Take the EMD calculation process as an example, F-IMF values of the ECG information may be calculated, square values may be calculated, and the square values may be normalized. Then a mean value and a variance value of the normalized values may be calculated. Afterwards, a mean value threshold and a variance value threshold may be set respectively and used for noise determination. The calculated mean value and the calculated variance may be compared with the mean value threshold and the variance value threshold. If the comparison result is within the scope of the threshold, it indicates that the ECG information includes noise(s) and the noise result may be output by the output module 230; if the comparison result is not within the scope of the threshold, it indicates that there is no noise in the ECG information and the noise result may be output by the output module 230.

Example 4

The power supply may be switched on and the acquisition module 210 may be initiated. After initialization and environment self-adaptation, the module may collect ECG information of a subject. The collected ECG information may include wave shape, time interval, frequency, phase, peak, valley, amplitude, etc. The acquired information may be stored in an internal storage device of the module, an independent storage module (not shown), or the cloud server 260. Afterwards, the analysis module 220 may read the ECG information from the storage device or the storage module, and pre-process the information to eliminate obvious noise(s) from the information through filtering. The pre-processed information may be simultaneously transmitted to the algorithm B module 520 and the algorithm C module 530. The information may be processed by using the built-in B-algorithm or C-algorithm. As described in example 2 and example 3, the process may include calculation, analysis, determination, and/or process. If one of the calculation result of the B-algorithm or a calculation result of the C-algorithm indicates that the information includes noise(s), it indicates that the information includes noise(s). The information may be transmitted to the processing module 540 to be processed for noise removal. Afterwards, the information with noise(s) removed may be output by the output module 230.

Example 5

The power supply may be switched on and the acquisition module 210 may be initiated. After initialization and environment self-adaptation, the module may collect ECG information of a subject. The collected ECG information may include wave shape, time interval, frequency, phase, peak, valley, amplitude, etc. The acquired information may be stored in an internal storage device of the module, an independent storage module (not shown), or the cloud server 260. Afterwards, the analysis module 220 may read the ECG information from the storage device or the storage module, and pre-process the information to eliminate obvious noise(s) from the information through filtering. The preprocessed ECG information may be transmitted to the algorithm A module 510. The algorithm A module 510 may determine a distribution type of the information, calculate a kurtosis of the information by using a built-in A algorithm, and generate a kurtosis calculation result. Then a noise threshold may be set according to the distribution type of the information. If the kurtosis calculation result is larger than the threshold value, it may indicate that there is no noise in the information, and a noise result that there is no noise in the information may be output by the output module 230. If the kurtosis calculation result is smaller than the threshold value, it may indicate that the information includes noise(s), and the noise(s) may be further recognized and removed. Then the information may be simultaneously transmitted to the algorithm B module 520 and the algorithm C module 530. The information may be processed by using the built-in B-algorithm or C-algorithm. As described in example 2 and example 3, the process may include calculation, analysis, determination, and/or process. If one of the calculation result of the B-algorithm or a calculation result of the C-algorithm indicates that the information includes noise(s), it indicates that the information includes noise(s). The information may be transmitted to the processing module 540 to be processed for noise removal. Afterwards, the information with noise(s) removed may be output by the output module 230.

The examples described above are only some embodiments of the present disclosure, the descriptions may be detailed but should not be considered as a limit to the scope of the present disclosure. It should be noted that persons having ordinary skills in the art may make many modifications and improvements without deviating the principle of the present disclosure, for example, new features or new combinations in the present disclosure, and steps of new methods or new combinations in the present disclosure, which are all within the scope of the present disclosure.

We claim:
1. A system, comprising:
   at least one storage medium including a set of instructions;
   at least one processor in communication with the at least one storage medium, wherein when executing the set of instructions, the at least one processor is configured to cause the system to:
      obtain electrocardiogram (ECG) information;
      detect peaks based on the ECG information using a first approach and a first threshold;
      detect a QRS wave based on the ECG information using a second approach, wherein the second approach is different from the first approach;
      perform a matching between the peaks and the QRS wave based on a distance between the QRS wave and a peak to be matched;
      determine a position of a matched peak in the peaks based on the performed matching;
      determine a peak within a first time interval after the position of the matched peak as a second peak corresponding to a T wave;
      determine a peak within a second time interval before the position of the matched peak as a third peak corresponding to a P wave;

obtain remainder peaks of the peaks by excluding the matched peak, the second peak, and the third peak;
perform a noise determination on the remainder peaks; and
output a result of the noise determination.

2. The system of claim 1, wherein to detect peaks based on the ECG information using a first approach and a first threshold, the at least one processor is configured to cause the system further to:
determine the first threshold;
determine an absolute value of the ECG information;
detect a local maximum value;
determine preliminary peaks based on the local maximum value;
compare the preliminary peaks with the first threshold; and
determine preliminary peaks larger than the first threshold as the peaks.

3. The system of claim 1, wherein the second approach comprises at least one of a threshold technique, a template matching technique, a wavelet transform technique, or a neural network technique.

4. The system of claim 1, wherein to perform a matching between the peaks and the QRS wave based on a distance between the QRS wave and a peak to be matched, the at least one processor is configured to cause the system further to:
determine a second threshold;
determine the distance between the QRS wave and the peak to be matched; and
in response to the determination that the distance is within the second threshold, determine the QRS wave is matched with the peak.

5. A method implemented on a computing device having at least one processor, at least one storage medium, and a communication platform connected to a network, the method comprising:
obtaining electrocardiogram (ECG) information;
detecting peaks based on the ECG information using a first approach and a first threshold;
detecting a QRS wave based on the ECG information using a second approach, wherein the second approach is different from the first approach;
performing a matching between the peaks and the QRS wave based on a distance between the QRS wave and a peak to be matched;
determining a position of a matched peak in the peaks based on the performed matching;
determining a peak within a first time interval after the position of the matched peak as a second peak corresponding to a T wave;
determining a peak within a second time interval before the position of the matched peak as a third peak corresponding to a P wave;
obtaining remainder peaks in the peaks by excluding the matched peak, the second peak, and the third peak;
performing a noise determination on the remainder peaks; and
outputting a result of the noise determination.

6. The method of claim 5, wherein the detecting peaks based on the ECG information using a first approach and a first threshold comprises:
determining the first threshold;
determining an absolute value of the ECG information;
detecting a local maximum value;
determining preliminary peaks based on the local maximum value;
comparing the preliminary peaks with the first threshold; and
determining preliminary peaks larger than the first threshold as the peaks.

7. The method of claim 5, wherein the second approach comprises at least one of a threshold technique, a template matching technique, a wavelet transform technique, or a neural network technique.

8. The method of claim 5, wherein performing a matching between the peaks and the QRS wave based on a distance between the QRS wave and a peak to be matched comprises:
determining a second threshold;
determining the distance between the QRS wave and the peak to be matched; and
in response to the determination that the distance is within the second threshold, determining the QRS wave is matched with the peak.

9. A non-transitory computer readable medium, comprising a set of instructions, wherein when executed by at least one processor, the set of instructions directs the at least one processor to perform acts of:
obtaining electrocardiogram (ECG) information;
detecting peaks based on the ECG information using a first approach and a first threshold;
detecting a QRS wave based on the ECG information using a second approach, wherein the second approach is different from the first approach;
performing a matching between the peaks and the QRS wave based on a distance between the QRS wave and a peak to be matched;
determining a position of a matched peak in the peaks based on the performed matching;
determining a peak within a first time interval after the position of the matched peak as a second peak corresponding to a T wave;
determining a peak within a second time interval before the position of the matched peak as a third peak corresponding to a P wave;
obtaining remainder peaks of the peaks by excluding the matched peak, the second peak, and the third peak;
performing a noise determination on the remainder peaks; and
outputting a result of the noise determination.

10. The non-transitory computer readable medium of claim 9, wherein the detecting peaks based on the ECG information using a first approach and a first threshold comprises:
determining the first threshold;
determining an absolute value of the ECG information;
detecting a local maximum value;
determining preliminary peaks based on the local maximum value;
comparing the preliminary peaks with the first threshold; and
determining preliminary peaks larger than the first threshold as the peaks.

11. The non-transitory computer readable medium of claim 9, wherein the second approach comprises at least one of a threshold technique, a template matching technique, a wavelet transform technique, or a neural network technique.

12. The non-transitory computer readable medium of claim 9, wherein performing a matching between the peaks and the QRS wave based on a distance between the QRS wave and a peak to be matched comprises:
determining a second threshold;
determining the distance between the QRS wave and the peak to be matched; and in response to the determination that the distance is within the second threshold, determining the QRS wave is matched with the peak.

* * * * *